United States Patent
Gross et al.

(10) Patent No.: US 7,931,858 B1
(45) Date of Patent: Apr. 26, 2011

(54) SYSTEM AND METHOD FOR SURFACE DECONTAMINATION USING ELECTROMAGNETIC SURFACE WAVES

(75) Inventors: Adam F. Gross, Los Angeles, CA (US); Kevin W. Kirby, Calabasas Hills, CA (US); Daniel J. Gregoire, Thousand Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 381 days.

(21) Appl. No.: 12/144,134

(22) Filed: Jun. 23, 2008

(51) Int. Cl.
*A61L 2/02* (2006.01)
(52) U.S. Cl. ............... 422/22; 422/21; 204/157.15
(58) Field of Classification Search .......... 422/21, 422/22; 204/157.15
See application file for complete search history.

(56) References Cited

U.S. PATENT DOCUMENTS

| | | | |
|---|---|---|---|
| 4,892,906 A | 1/1990 | Pham et al. | |
| 5,650,461 A | 7/1997 | Wasserman et al. | |
| 6,245,126 B1 * | 6/2001 | Feldman et al. | 95/59 |
| 6,531,537 B2 | 3/2003 | Friel et al. | |
| 2003/0165636 A1 * | 9/2003 | Koulik et al. | 427/569 |
| 2004/0042077 A1 | 3/2004 | Birge et al. | |
| 2004/0164682 A1 | 8/2004 | Hopwood et al. | |
| 2004/0175407 A1 | 9/2004 | McDaniel | |
| 2004/0224145 A1 | 11/2004 | Weir et al. | |
| 2004/0256056 A1 | 12/2004 | Hall et al. | |
| 2005/0058689 A1 | 3/2005 | McDaniel | |
| 2005/0126441 A1 | 6/2005 | Skelhorn | |
| 2006/0141003 A1 | 6/2006 | McDaniel | |

OTHER PUBLICATIONS

Daniels, "On the Ionization of Air for Removal of Noxious Effluvia (Air Ionization of Indoor Environments for Control of Volatile and Particulate Contaminants with Nonthermal Plasmas Generated by Dielectric-Barrier Discharge," IEEE Transactions on Plasma Science, vol. 30, No. 4, Aug. 2002, pp. 1471-1481.

Deng, et al., "Physical Mechanisms of Inactivation of *Bacillus subtilis* Spores Using Cold Atmospheric Plasmas," IEEE Transactions on Plasma Science, vol. 34, No. 4, Aug. 2006, pp. 1310-1316.

Herrmann, et al., "Chemical Warfare Agent Decontamination Studies in the Plasma Decon Chamber," IEEE Transactions on Plasma Science, vol. 30, No. 4, Aug. 2002, pp. 1460-1470.

Laroussi, "Nonthermal Decontamination of Biological Media by Atmospheric-Pressure Plasmas: Review, Analysis, and Prospects," IEEE Transactions on Plasma Science, vol. 30, No. 4, Aug. 2002, pp. 1409-1415.

Montie, et al., "An Overview of Research Using the One Atmosphere Uniform Glow Discharge Plasma (OAUGDP) for Sterilization of Surfaces and Materials," IEEE Transactions on Plasma Science, vol. 28, No. 1, Feb. 2000, pp. 41-50.

* cited by examiner

*Primary Examiner* — Sean E Conley
(74) *Attorney, Agent, or Firm* — Christie, Parker, Hale

(57) ABSTRACT

A method of decontaminating a surface is provided. A surface to propagate electromagnetic surface waves is provided having a frequency in the microwave spectrum between 1 GHz and 1000 GHz. The surface includes a surface-wave medium or the surface-wave medium is laminated on the surface for confining the electromagnetic surface waves to the surface. The surface-wave medium includes a conductive ground plane. A dielectric is provided on the ground plane. A metallic pattern is provided on the dielectric for increasing an inductive reactance of the surface-wave medium. Electromagnetic surface waves are transmitted onto the surface from a surface-wave coupler coupled to the surface for destroying, removing, or neutralizing chemical or biological surface contaminants. The surface contaminants are destroyed, removed, or neutralized with a plasma created by the electromagnetic surface waves or through absorption of the electromagnetic surface waves.

15 Claims, 8 Drawing Sheets

SYSTEM AND METHOD FOR SURFACE DECONTAMINATION USING ELECTROMAGNETIC SURFACE WAVES

CROSS-REFERENCE TO RELATED APPLICATION(S)

This application is related to the following patent applications, all of which are incorporated herein by reference: H611:60258 entitled "System and Method of Surface Wave Imaging to Map Pressure on a Surface"; H611:60448 entitled "System and Method of Surface Wave Imaging to Detect Ice on a Surface"; H611:60449 entitled "System and Method of Surface Wave Imaging to Detect Damage to a Surface"; H611:60592 entitled "Method for De-icing Using Electromagnetic Surface Waves"; and H611:60447 entitled "System and Method for Large Scale Atmospheric Plasma Generation." This application is also related to U.S. Pat. No. 7,307,589 entitled "Large-Scale Adaptive Surface Sensor Arrays," which is incorporated herein by reference.

BACKGROUND OF THE INVENTION

1. Field of the Invention

The present invention relates to electromagnetic surface waves, and in particular, a method for decontaminating a surface using electromagnetic surface waves.

2. Description of Related Art

U.S. Pat. No. 6,531,537 entitled "Prepaints and methods of preparing paints from the prepaints," U.S. Pat. No. 5,650,461 entitled "Paint compositions for high infra-red reflectivity with a low gloss property," U.S. Pat. No. 4,892,906 entitled "Urethane coating composition," and U.S. patent application Ser. No. 10/989,120 entitled "Composition of a thermaly insulating coating system," all of which are incorporated herein by reference, disclose a paint that may be used as a chemical agent resistant coating. The chemical resistance coating is designed to be treated with deactivating chemicals and will not protect itself from chemical or biological warfare agents.

U.S. patent application Ser. No. 10/429,687 entitled "Self-decontaminating or self-cleaning coating for protection against hazardous bio-pathogens and toxic chemical agents," which is incorporated herein by reference, covers "A self-cleaning, self-decontaminating coating capable of producing hydroxyl radicals, in the presence of UV radiation and moisture, in sufficient amounts to destroy organic contaminants on the coating surface." U.S. patent application Ser. No. 11/368,086 entitled "Antifungal paints and coatings," U.S. patent application Ser. No. 10/884,355 entitled "Antifungal paints and coatings," U.S. patent application Ser. No. 10/792,516 entitled "Microorganism coating components, coatings, and coated surfaces," and U.S. patent application Ser. No. 10/655,345 entitled "Biological active coating components, coatings, and coated surfaces," all of which are incorporated herein by reference, use enzymes trapped in a coating to deactivate chemical weapons agents, pesticides, and kill bacteria and fungus. The enzymes are not effective against mustard gas and the efficacy of the enzymes for killing bacteria is unknown. In addition, when all the enzymes are consumed, the coating will not continue to be effective. U.S. patent application Ser. No. 10/491,776 entitled "Microwave plasma generator," which is incorporated herein by reference, discloses use of a microwave created plasma in an air duct to destroy chemical weapons. U.S. patent application Ser. No. 10/743,124 entitled "Low power plasma generator," which is incorporated herein by reference, discloses a small size microwave plasma generator that can be used to destroy chemical weapons.

Further prior art related to plasmas include H. W. Herrmann, G. S. Selwyn, I. Henins, J. Park, M. Jeffery, and J. M. Williams, "Chemical Warfare Agent Decontamination Studies in the Plasma Decon Chamber," IEEE Transactions on Plasma Science, Vol. 30, No. 4, August 2002, p. 1460; T. C. Montie, K. Kelly-Wintenberg, and J. R. Roth, "An Overview of Research Using the One Atmosphere Uniform Glow Discharge Plasma (OAUGDP) for Sterilization of Surfaces and Materials," IEEE Transactions on Plasma Science, Vol. 28, No. 1, February 2000, p. 41; M. Laroussi, "Nonthermal Decontamination of Biological Media by Atmospheric-Pressure Plasmas: Review, Analysis, and Prospects," IEEE Transactions on Plasma Science, Vol. 30, No. 4, August 2002, p. 1409; X. Deng, J. Shi, M. G. Kong, "Physical Mechanisms of Inactivation of *Bacillus subtilis* Spores Using Cold Atmospheric Plasmas," IEEE Transactions on Plasma Science, Vol. 34, No. 4, August 2006, p. 1310; and S. L. Daniels, "On the Ionization of Air for Removal of Noxious Effluvia (Air Ionization of Indoor Environments for Control of Volatile and Particulate Contaminants with Nonthermal Plasmas Generated by Dielectric-Barrier Discharge," IEEE Transactions on Plasma Science, Vol. 30, No. 4, August 2002, p. 1471, all of which are incorporated herein by reference.

While conventional decontamination solutions are effective at destroying the contaminant, large volumes of reactive chemicals must be transported to the contaminated vehicle and the solution may damage sensitive surfaces. In addition, the chemicals must be available for application and the surface must be coated with a chemical agent resistant coating. All of the requirements for decontamination require additional logistics and special chemical handling. Therefore, a need exists for a decontamination process that is simple and fast and that requires no supplied chemicals or chemical clean-up.

SUMMARY OF THE INVENTION

A method of decontaminating a surface is provided. The surface is provided to propagate electromagnetic surface waves. The electromagnetic surface waves are transmitted onto the surface for destroying, removing, or neutralizing chemical or biological surface contaminants.

In one exemplary embodiment, the electromagnetic surface waves have a frequency in the microwave spectrum between 1 GHz and 1000 GHz.

In one exemplary embodiment, a plasma is created on the surface by transmitting the electromagnetic surface waves having a power sufficient for creating the plasma on the surface. The surface contaminants are destroyed, removed, or neutralized using the plasma through chemical reaction, thermal dissociation, or energetic transitions of the surface contaminants.

In one exemplary embodiment, the surface contaminants are destroyed, removed, or neutralized through resonant absorption of the electromagnetic surface waves by the surface contaminants.

In one exemplary embodiment, the surface includes a surface-wave medium for confining the electromagnetic surface waves to the surface. The surface-wave medium includes a conductive ground plane, a dielectric on the ground plane, and a metallic pattern on the dielectric for increasing an inductive reactance of the surface-wave medium.

In one exemplary embodiment, a surface-wave medium is laminated on the surface for confining the electromagnetic surface waves to the surface. The surface-wave medium includes a conductive ground plane, a dielectric on the ground plane, and a metallic pattern on the dielectric for increasing an inductive reactance of the surface-wave medium.

In one exemplary embodiment, the electromagnetic surface waves are transmitted from a surface-wave coupler coupled to the surface.

In one exemplary embodiment, the metallic pattern is a repeating pattern of Jerusalem crosses.

In one exemplary embodiment, the dielectric is a flexible dielectric sheet having a thickness equal to or less than 0.01 inch.

In one exemplary embodiment, the surface is an electrical conductor.

In one exemplary embodiment, the surface is a non-conductor.

In an exemplary embodiment of the present invention, a method of decontaminating a surface is provided including providing the surface to propagate electromagnetic surface waves having a frequency in the microwave spectrum between 1 GHz and 1000 GHz. The surface includes a surface-wave medium for confining the electromagnetic surface waves to the surface, the surface-wave medium including a conductive ground plane, a dielectric on the ground plane, and a metallic pattern on the dielectric for increasing an inductive reactance of the surface-wave medium. The method includes transmitting electromagnetic surface waves onto the surface from a surface-wave coupler coupled to the surface for destroying, removing, or neutralizing chemical or biological surface contaminants; and destroying, removing, or neutralizing the surface contaminants using a plasma created by the electromagnetic surface waves or through absorption of the electromagnetic surface waves.

In one exemplary embodiment, the surface-wave medium is laminated on the surface.

In one exemplary embodiment, the electromagnetic surface waves have a frequency of about 2.45 GHz.

In one exemplary embodiment, the transmitted electromagnetic surface waves have a frequency substantially identical to the resonant frequency of the surface contaminants.

In an exemplary embodiment of the present invention, a process for decontaminating a surface is provided including modifying the surface prior to contamination by laminating a surface-wave medium to the surface; coupling a surface wave coupler to the surface; and transmitting electromagnetic surface waves from the surface wave coupler to the surface.

In an exemplary embodiment of the present invention, an apparatus for facilitating decontamination of a surface is provided including the surface and a surface wave coupler; wherein the surface further comprises a surface-wave medium laminated to the surface.

In one exemplary embodiment, the surface-wave medium further comprises a dielectric and a metallic pattern on the dielectric for increasing the inductive reactance of the surface-wave medium.

In one exemplary embodiment, the surface-wave medium further comprises a conductive ground plane, a dielectric and a metallic pattern on the dielectric for increasing the inductive reactance of the surface-wave medium.

DETAILED DESCRIPTION

In the description below, an introduction to electromagnetic surface-wave technology, including surface-wave communication and power technology is provided. Methods are then provided for decontaminating a surface.

Figure 1:
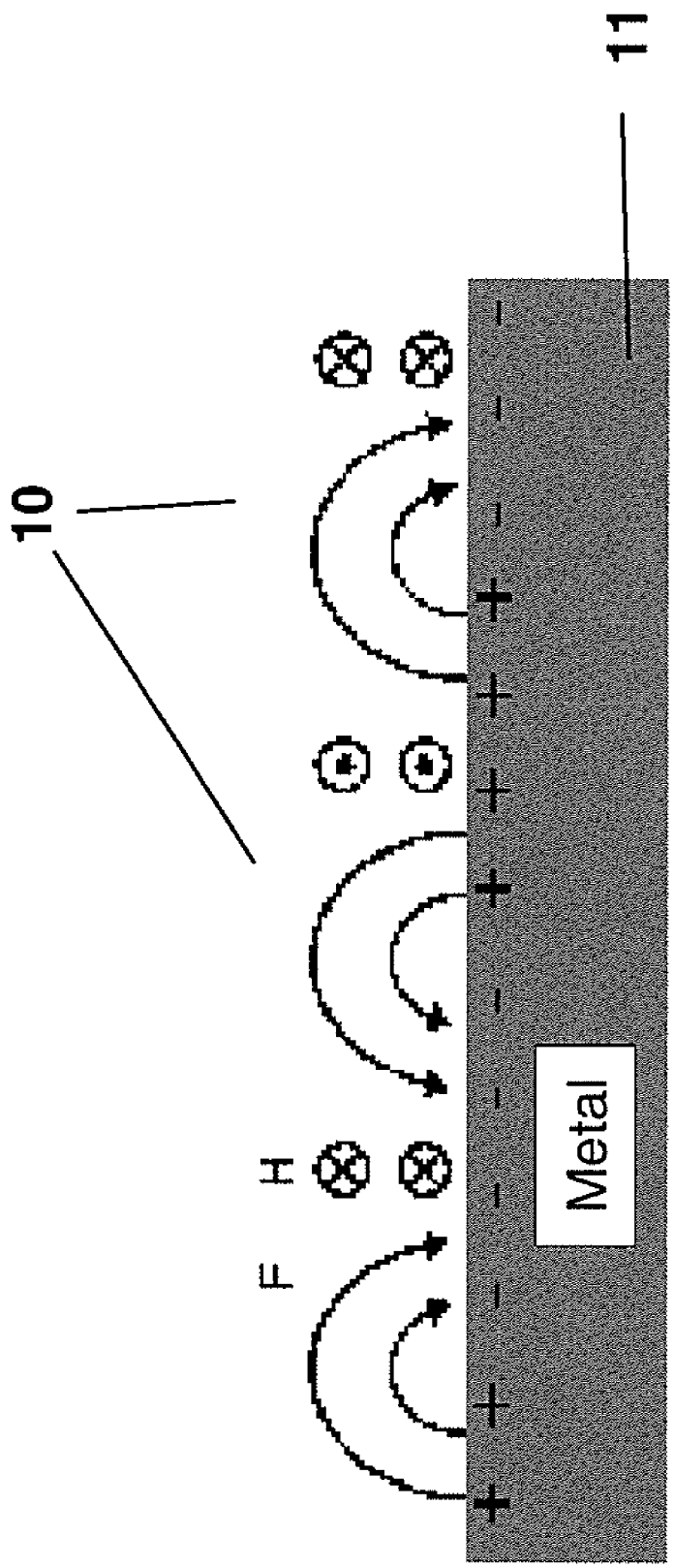
FIG. 1 depicts fields of a transverse magnetic surface wave on a flat metal surface.

FIG. 1 depicts a transverse magnetic (TM) surface wave 10 on a flat metal surface 11. A TM wave requires a surface with a surface impedance having an inductive term, while, in order to support a transverse electric (TE) surface wave, the reactive part of the surface impedance must be capacitive.

At optical frequencies, surface waves are known as surface plasmons. Surface waves are waves that are bound to the interface between a metal or other material and the surrounding space. The surface waves are characterized by longitudinally oscillating charges on the metal surface and associated fields in free space. On a flat metal surface, surface waves typically extend many thousands of wavelengths into the surrounding space. At low microwave frequencies, surface waves can extend many hundreds of meters into the surrounding space. Surfaces that allow surface waves to extend too far out into the surrounding space are not useful for wave guiding. Traditional techniques for creating surface wave media that confine fields closer to the surface generally involve thick dielectric coatings, which are not suitable for many military applications. Recent research has shown, however, that it is possible to produce thin, light-weight structures with textured-impedance surfaces that can have strong surface-wave guiding effects where the fields are confined close to the surface, do not readily leak power into free space, can follow curves in the surface, and have negligible propagation loss.

Figure 2:
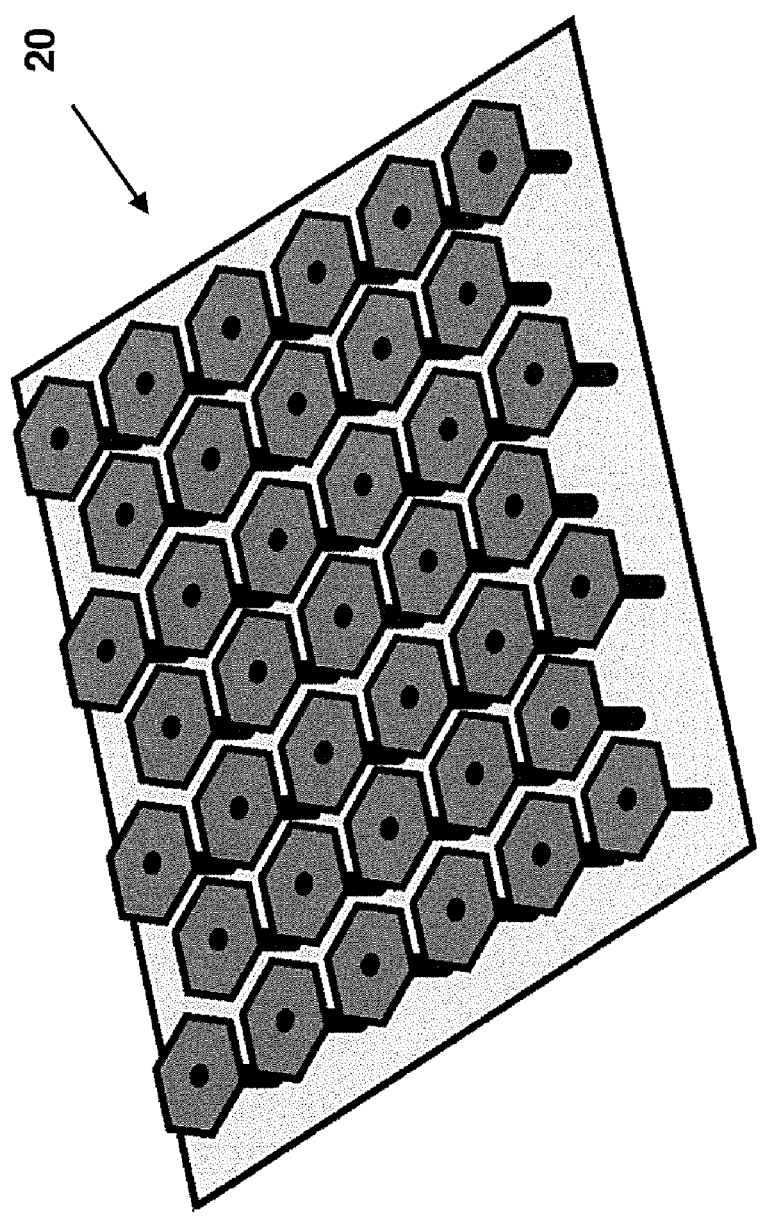
FIG. 2 depicts a periodic frequency-selective surface-wave guide having high impedance.
Figure 3:
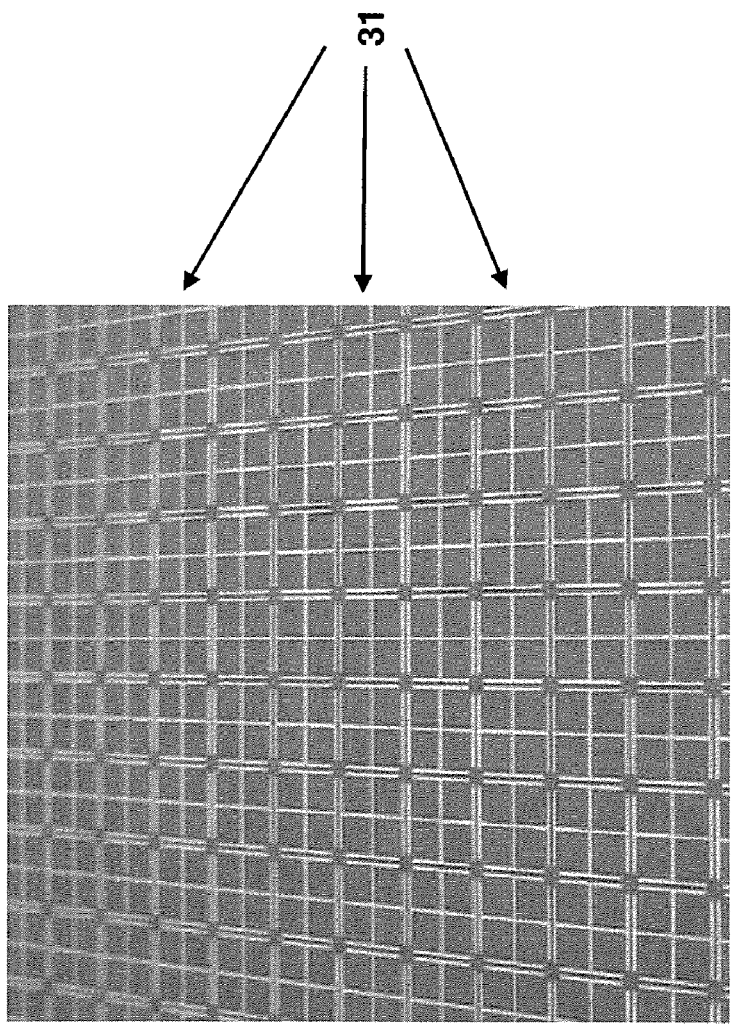
FIG. 3 depicts another periodic frequency-selective surface-wave guide having an array of Jerusalem Crosses.

FIG. 2 and FIG. 3 are two examples of textured-impedance surface geometries. A textured-impedance surface typically consists of a series of resonant structures tiled onto a thin flexible substrate. The complex geometry creates a medium that supports highly localized surface wave propagation by altering the surface impedance, such that the decay constant into free space is rapid, thus binding the wave to less than within a wavelength of the surface. A closely bound surface wave may be propagated along the surface with a small attenuation if the inductive reactance (i.e., reactive part of the surface impedance) is large and the resistance (i.e., real part of the surface impedance) is small. FIG. 2 depicts a two-layer high impedance surface-wave guide 20. FIG. 3 depicts a periodic frequency-selective surface-wave guide 30 having an array of Jerusalem Crosses 31. The surfaces depicted in FIG. 2 and FIG. 3 are inexpensive to manufacture and are readily integrated within structures.

Figure 4:
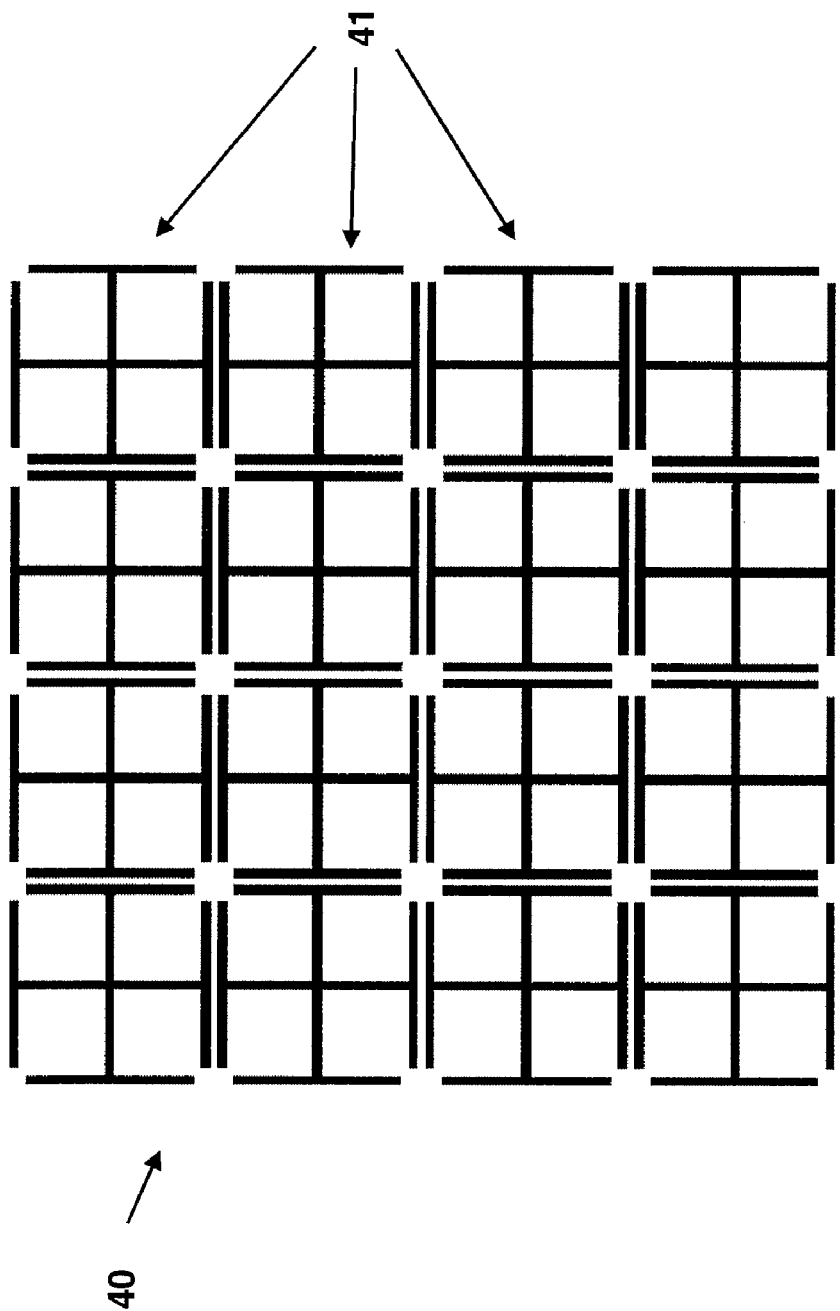
FIG. 4 is a schematic of an array of Jerusalem Crosses.
Figure 5:
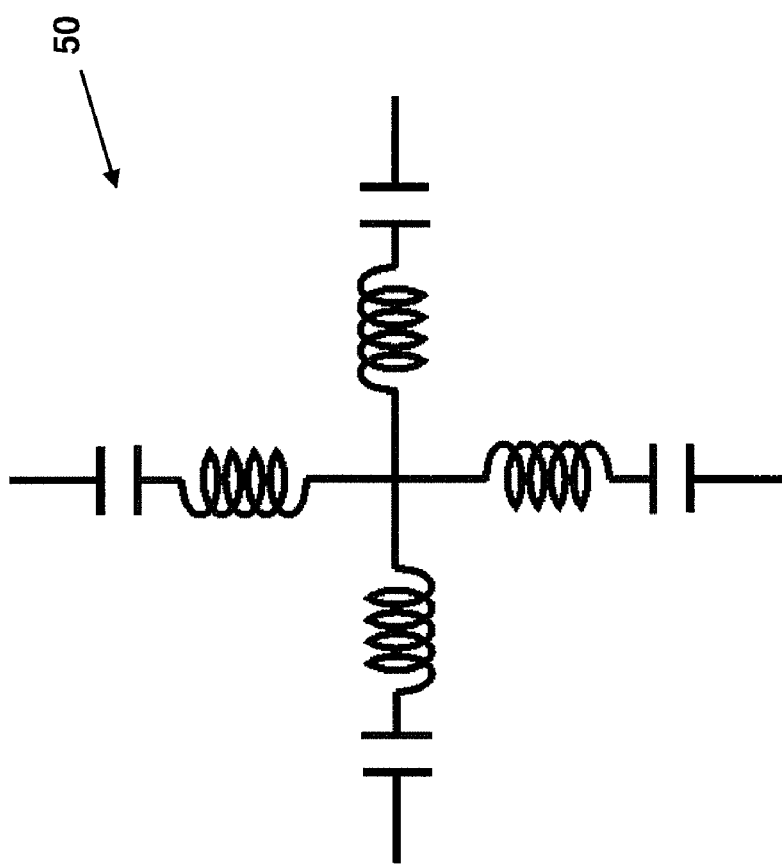
FIG. 5 is a circuit diagram depicting the equivalent circuit for the frequency selective surface-wave guide of FIG. 3.

FIG. 4 is a schematic of an array 40 of Jerusalem Crosses 41. FIG. 5 is a circuit diagram depicting the equivalent circuit for the frequency selective surface-wave guide 30 of FIG. 3.

Figure 6:
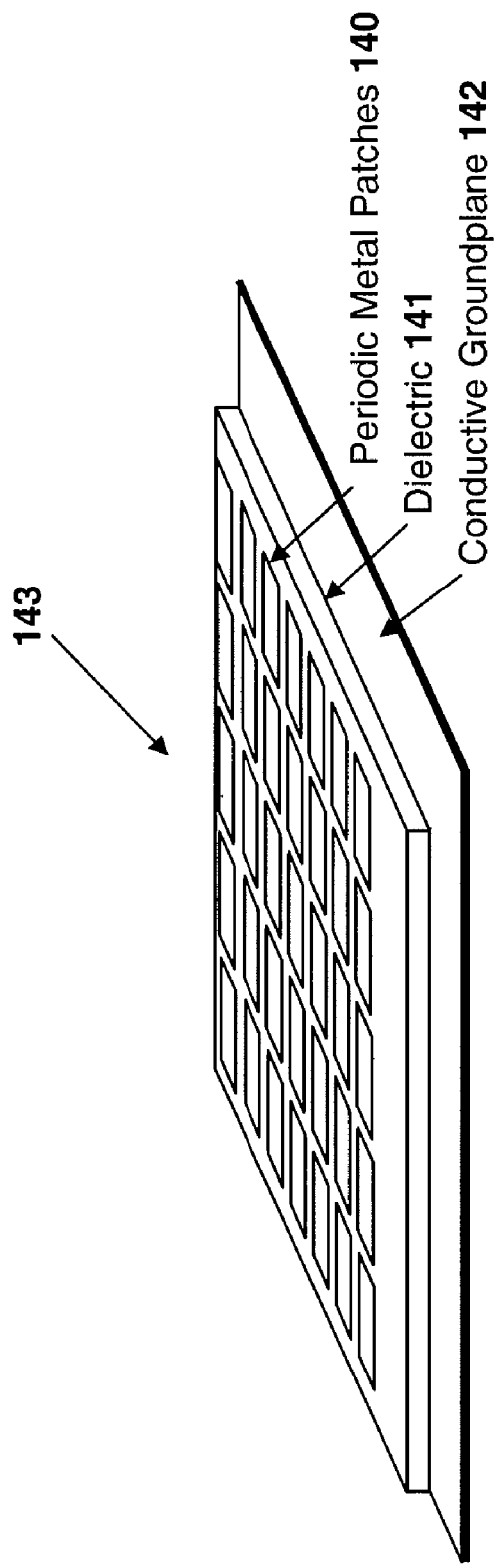
FIG. 6 depicts a surface-wave medium.
Figure 7:
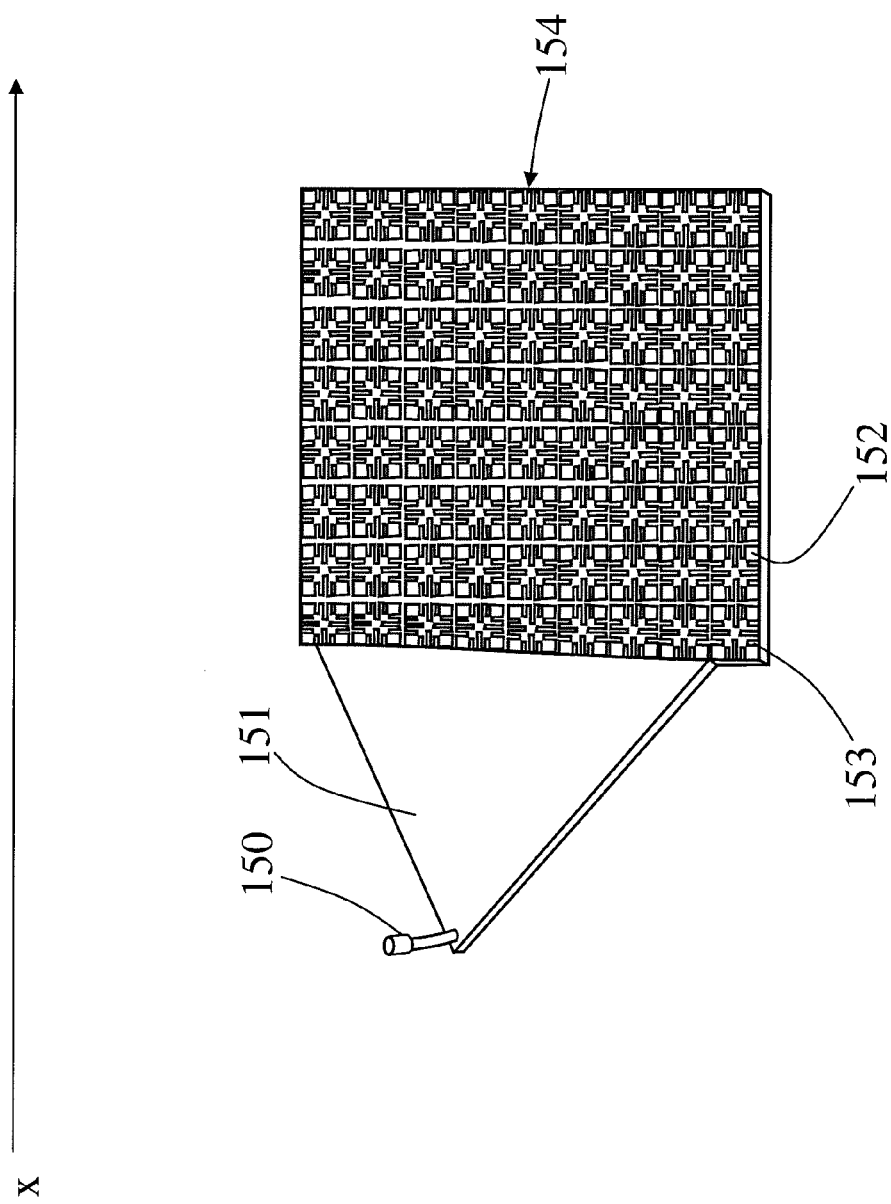
FIG. 7 depicts a high power surface-wave coupler integrated to a surface-wave medium for surface decontamination.
Figure 8:
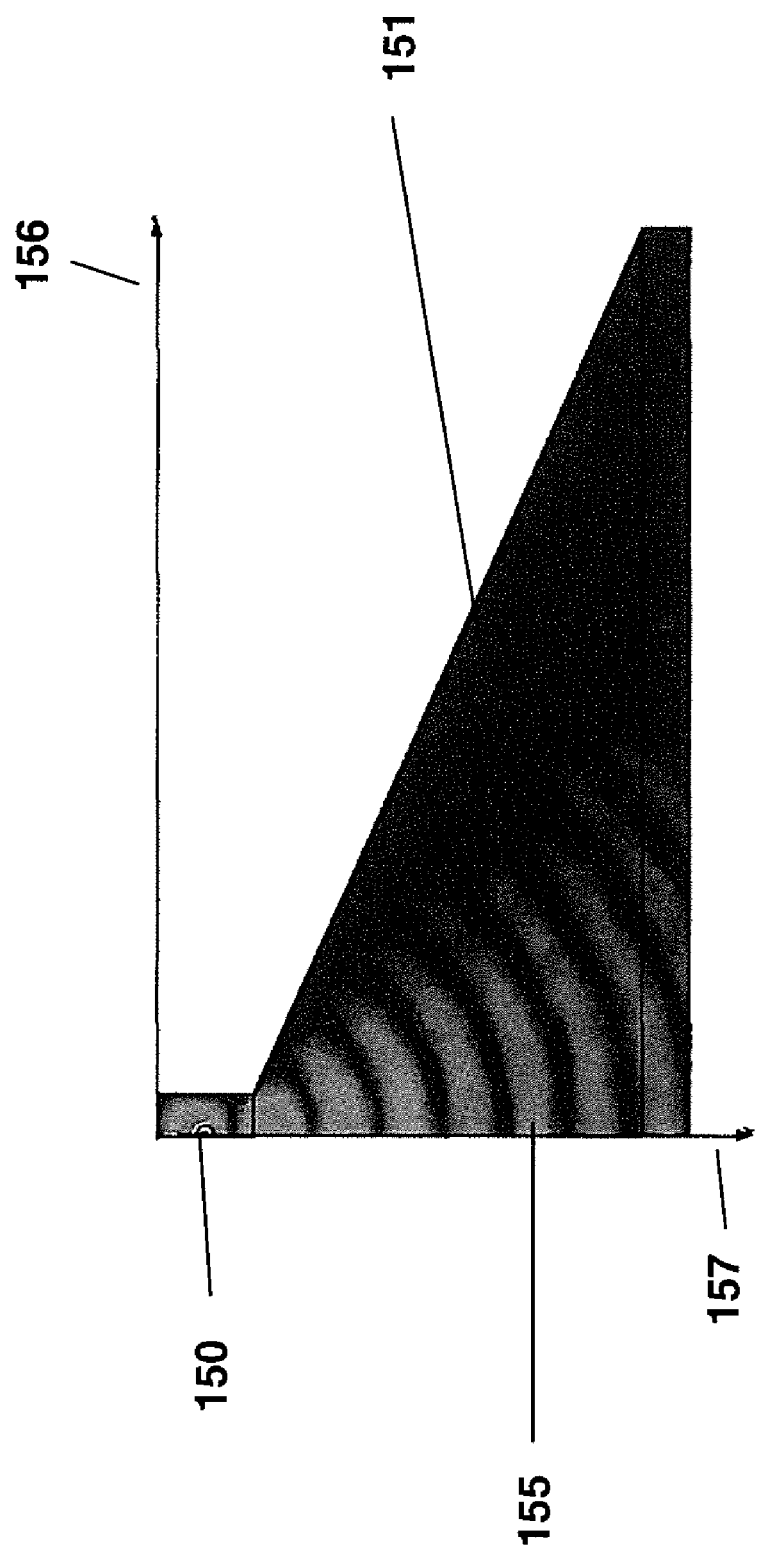
FIG. 8 depicts field patterns in the surface wave coupler.

FIG. 6 depicts a surface-wave medium. FIG. 7 depicts a high power surface-wave coupler 151 integrated to a surface-wave medium 154. FIG. 8 depicts field patterns 155 in the surface-wave coupler 151. In an exemplary embodiment of the present invention, a system and a method for delivering microwave energy to a target contaminant on a surface of a structure is provided. Unlike a conventional microwave oven where energy is provided from a point source radiating in three dimensions, the system creates a two-dimensional wave of energy that is confined to a contaminated surface. In an exemplary embodiment, the the surface-wave medium 154 is built into the surface. In an alternative embodiment, the system is achieved using a specialized surface laminate that supports a surface wave of high-power microwave energy. The surface may be an electrical conductor or may be a non-conductor. The thin laminate is mated to the underlying host surface to form a unitized monolithic structure. The high-power surface wave is launched at a given source location on the surface of the structure and propagates simultaneously over its entire area.

In an exemplary embodiment, the surface wave creates a localized high energy plasma that destroys, removes, or neutralizes the resident contamination through chemical reaction, thermal dissociation, or energetic transitions of the target species. The surface plasma consists of reactive ionic and free radical species that destructively interact with the target contaminant. In another exemplary embodiment, the destruction, removal, or neutralization of the contamination is achieved through resonant absorption of the surface microwaves by the target species. Direct absorption of the microwaves leads to thermal dissociation or structural alteration of the target species as a means for eliminating the chemical or biological threat.

Chemical or biological contamination threatens military vehicles, warfighters, and commercial aircraft. The contamination may be caused by a terrorist attack, attack from an opposing military force, or by a naturally occurring airborne disease. A conventional method of neutralizing chemical or biological agents is to spray the contaminated vehicle with caustic oxidizing solutions. While these solutions are effective at destroying the contaminant, large volumes of reactive chemicals must be transported to the contaminated vehicle and the solution may damage sensitive surfaces. In addition, the chemicals must be available for application and the surface must be coated with a chemical agent resistant coating. All of the requirements for decontamination require additional logistics and special chemical handling.

In the exemplary embodiments, the decontamination process is simple and fast and requires no supplied chemicals or chemical clean-up. Use of surface-waves for decontamination requires a power source and a microwave source (e.g., magnetron) to remediate contamination on the specialized structures. The system may be integrated with an on-board power source or be adapted for connection to an external power source that can be easily transported.

In an exemplary embodiment, a system and a method for destroying, removing, or otherwise neutralizing chemical or biological contamination residing on the surface of a structure using microwave energy is provided. The system and method are realized by laminating a surface with a surface-wave medium capable of supporting the propagation of tightly bound electromagnetic surface waves across it. The surface waves are launched into the surface-wave medium and propagate across the surface-wave medium and spread out to cover the entire surface.

Typically, a surface-wave medium 143 can be realized by a reactive impedance surface. Reactive impedance surfaces can be formed by laminating textured metallic patterns 140 to an insulating dielectric 141 on top of a metallic ground plane 142. The surface impedance is determined by the thickness of the dielectric 141 and its electrical properties, such as its permittivity, resistivity and permeability. The simplest metallic pattern 140 is a periodic arrangement of metallic squares. The size of the squares and their spacing determines the magnitude of surface's reactive impedance. The magnitude of the impedance determines how tightly a surface wave is bound to the surface-wave medium 143.

In an exemplary embodiment, the surface-wave medium is capable of supporting high-power microwave-frequency surface waves between 1 GHz and 1000 GHz (i.e., in the microwave spectrum). The most convenient microwave frequency to design for is 2.45 GHz because high-power (~1 kW), inexpensive, and commercially available magnetron sources are available at this frequency. Microwaves at other frequencies more effective for destroying, removing, or neutralizing chemical or biological threats may also be employed. In addition, the surface-wave medium is tolerant of damage, contamination, and faults. If a break, rip, or tear appears in the surface-wave medium, the surface-wave medium will still propagate the surface waves and it will still operate over the unaffected sections.

As depicted in FIG. 7 and FIG. 8, a surface wave can be launched into the surface-wave medium 154 with a surface-wave coupler 151. The parallel plate waveguide coupler 151 is fed with microwave energy via a coaxial input cable 150 or with a waveguide. The parallel plate portion of the waveguide coupler is mated to the surface-wave medium 154 in thickness (i.e., both the coupler 151 and surface-wave medium 154 extend in the x direction as depicted in FIG. 7) so that there is very low insertion loss between the coupler 151 and the surface-wave medium 154.

In FIG. 7, a high power surface is excited in the surface-wave medium 154 with a coupler 151 that is fed by a microwave coaxial feed 150. The coupler 151 is a parallel plate waveguide structure that flares out to spread the surface wave before reaching the surface-wave medium 154. The surface-wave medium 154 is formed by a periodic pattern of metallization 153 on a dielectric sheet 152 of Kapton®. The metallic pattern 153 creates a complex surface impedance and may be a repeating pattern of Jerusalem crosses. The dielectric 152 can be flexible and layered onto a metallic ground plane having a thickness of 0.01 inches or less. In FIG. 8, the microwave power launched into a surface-wave coupler 151 spreads out to form a large cross section wave front 155 before being coupled into the surface-wave medium 154. The horizontal axis 156 is the horizontal spread of the surface wave. The vertical axis 157 is the vertical spread of the surface wave.

The preceding paragraphs describe structures for implementing a surface-wave medium. However, a person skilled in the art will realize a surface-wave medium may be constructed in other ways now known or in others ways yet to be developed. Consequently, a surface-wave medium should be interpreted as any surface capable of supporting surface waves, unless otherwise limited.

The use of microwaves or a plasma to destroy chemical and biological warfare agents is well documented in the scientific literature. For example, J. A. Starets in "Electronics and Radiophysics of Ultra-High Frequencies," 1999, International University Conference Proceedings on pages 479-480, which is incorporated herein by reference, shows microwave destruction of chemical warfare agents. The abstract discusses research work dealing with the effects microwaves exert on different substances, including chemical weapon agents (CWAs). The first stage of investigation included tests with a surrogate CWA and the results have shown that microwave energy at 2.45 GHz is most effectively absorbed by organophosphorus agents (OPA). Tributylphosphate (TBP) was used as the surrogate CWA. The tests with TBP revealed that the substance was being disintegrated by absorbed microwave energy. These tests proved the high efficacy of the method. Energy consumption was 2 kWh per 1 kg of the agent.

Additional work by H. W. Herrmann, I. Henins, J. Park, and G. S. Selwyn in Physics of Plasmas, 6. (1999) 2284, which is incorporated herein by reference, shows the use of a plasma jet to destroy chemical and biological weapons agents. The plasma is a room temperature plasma that creates reactive gas species that destroy contaminants.

While the invention has been described in terms of exemplary embodiments, it is to be understood that the words which have been used are words of description and not of limitation. As is understood by persons of ordinary skill in the art, a variety of modifications can be made without departing from the scope of the invention defined by the following claims, which should be given their fullest, fair scope.

What is claimed is:

1. A method of decontaminating a surface, comprising:
   providing the surface to propagate electromagnetic surface waves; and
   transmitting the electromagnetic surface waves onto the surface for destroying, removing, or neutralizing chemical or biological surface contaminants,
   wherein a surface-wave medium is directly on the surface for confining the electromagnetic surface waves to the surface, the surface-wave medium including a dielectric and a metallic pattern on the dielectric for increasing an inductive reactance of the surface-wave medium.

2. The method as claimed in claim 1, wherein the electromagnetic surface waves have a frequency in the microwave spectrum between 1 GHz and 1000 GHz.

3. The method as claimed in claim 1, further comprising:
   creating a plasma on the surface by transmitting the electromagnetic surface waves having a power sufficient for creating the plasma on the surface; and
   destroying, removing, or neutralizing the surface contaminants using the plasma through chemical reaction, thermal dissociation, or energetic transitions of the surface contaminants.

4. The method as claimed in claim 1, wherein the surface contaminants are destroyed, removed, or neutralized through resonant absorption of the electromagnetic surface waves by the surface contaminants.

5. The method as claimed in claim 1, wherein the surface-wave medium further includes a conductive ground plane, the dielectric is on the ground plane, and the metallic pattern is on the dielectric.

6. The method as claimed in claim 1, further comprising:
   transmitting the electromagnetic surface waves from a surface-wave coupler coupled to the surface.

7. The method as claimed in claim 1, wherein the metallic pattern is a repeating pattern of Jerusalem crosses.

8. The method as claimed in claim 1, wherein the dielectric is a flexible dielectric sheet having a thickness equal to or less than 0.01 inch.

9. The method as claimed in claim 1, wherein the surface is an electrical conductor.

10. The method as claimed in claim 1, wherein the surface is a non-conductor.

11. A method of decontaminating a surface, comprising:
    providing the surface to propagate electromagnetic surface waves having a frequency in the microwave spectrum between 1 GHz and 1000 GHz;
    wherein the surface includes a surface-wave medium for confining the electromagnetic surface waves to the surface, the surface-wave medium including a conductive ground plane, a dielectric on the ground plane, and a metallic pattern on the dielectric for increasing an inductive reactance of the surface-wave medium;
    transmitting electromagnetic surface waves onto the surface from a surface-wave coupler coupled to the surface for destroying, removing, or neutralizing chemical or biological surface contaminants; and
    destroying, removing, or neutralizing the surface contaminants using a plasma created by the electromagnetic surface waves or through absorption of the electromagnetic surface waves.

12. The method of claim 11, wherein the surface-wave medium is laminated on the surface.

13. The method of claim 11, wherein the electromagnetic surface waves have a frequency of about 2.45 GHz.

14. The method of claim 11, wherein the transmitted electromagnetic surface waves have a frequency substantially identical to the resonant frequency of the surface contaminants.

15. A process for decontaminating a surface comprising:
    modifying the surface prior to contamination by laminating a surface-wave medium to the surface, the surface-wave medium including a conductive ground plane, a dielectric on the ground plane, and a metallic pattern on the dielectric for increasing an inductive reactance of the surface-wave medium;
    coupling a surface-wave coupler to the surface; and
    transmitting electromagnetic surface waves from the surface-wave coupler to the surface to decontaminate the surface.

* * * * *